(12) United States Patent
Yamada et al.

(10) Patent No.: US 6,696,182 B2
(45) Date of Patent: Feb. 24, 2004

(54) ORGANIC ELECTROLUMINESCENT DEVICE COMPRISING DIPYRIDYLTHIOPHENE DERIVATIVE

(75) Inventors: Hiroshi Yamada, Yokohama (JP); Manabu Uchida, Yokohama (JP); Takaharu Nakano, Yokohama (JP); Kenji Furukawa, Yokohama (JP)

(73) Assignee: Chisso Corporation, Osaka (JP)

( * ) Notice: Subject to any disclaimer, the term of this patent is extended or adjusted under 35 U.S.C. 154(b) by 93 days.

(21) Appl. No.: 09/938,546

(22) Filed: Aug. 27, 2001

(65) Prior Publication Data

US 2002/0034658 A1 Mar. 21, 2002

(30) Foreign Application Priority Data

Sep. 7, 2000 (JP) .......................... 2000-271608

(51) Int. Cl.⁷ .......................... H05B 33/12; C09K 11/06; C07D 49/14
(52) U.S. Cl. ...................... 428/690; 428/917; 313/504; 252/301.16; 546/256
(58) Field of Search ............................ 428/690, 917; 313/502, 504, 506; 252/301.16; 546/256

(56) References Cited

U.S. PATENT DOCUMENTS 6,195,142 B1 * 2/2001 Gyotoku et al. ............... 349/69

FOREIGN PATENT DOCUMENTS

| DE | 25 34 713 | 2/1977 |
|---|---|---|
| EP | 0 668 277 | 8/1995 |
| EP | 0 853 083 | 7/1998 |
| JP | 57-144558 | 9/1982 |
| JP | 59-194393 | 11/1984 |
| JP | 61-062038 | 3/1986 |
| JP | 61-112164 | 5/1986 |
| JP | 61-124949 | 6/1986 |
| JP | 61-134354 | 6/1986 |
| JP | 61-134355 | 6/1986 |
| JP | 04-212286 | 8/1992 |
| JP | 04-308688 | 10/1992 |
| JP | 04-363891 | 12/1992 |
| JP | 05-152027 | 6/1993 |
| JP | 05-202011 | 8/1993 |
| JP | 05-343184 | 12/1993 |
| JP | 06-001972 | 1/1994 |
| JP | 06-020716 | 1/1994 |
| JP | 06-092947 | 4/1994 |
| JP | 06-136359 | 5/1994 |
| JP | 06-145658 | 5/1994 |
| JP | 06-267658 | 9/1994 |
| JP | 06-271843 | * 9/1994 |
| JP | 06-312979 | 11/1994 |
| JP | 07-090256 | 4/1995 |
| JP | 07-097355 | 4/1995 |
| JP | 07126226 | 5/1995 |
| JP | 07-126615 | 5/1995 |
| JP | 07-258537 | 10/1995 |
| JP | 07-331288 | 12/1995 |
| JP | 08-048656 | 2/1996 |
| JP | 08-100172 | 4/1996 |
| JP | 09-087616 | 3/1997 |
| JP | 11-345686 | 12/1999 |

OTHER PUBLICATIONS

Atkinson, R.E. and P.R.H. Speakman, "Synthesis and Emission Characteristics of Some Fluorescent Derivatives of 2–(2–Quinolyl)thiophen", Journal of the Chemical Society (Section B): Physical Organic (10), 2077–81 (English), 1971.*

Journal of the Chemical Society, Chemical Communications, vol. 17, pp. 1210–1212, (1991).*

Shizuoka Daigaku Denshi Kogaku Kenkyusho Kenkyo Hokotu, vol. 36, pp. 35–42, (2001).*

Abstract of JP 05 070455 (Mar. 1993), Patent Abstracts of Japan, vol. 17, No. 391 (Jul. 1993).

Naka, S., et al. "White Organic Electroluminescent Devices with Mixed Single Layer", IEICE Trans. Electron., vol. E80–C, No. 8 (1997), pp. 1114–1116.

Tang, C.W., et al. "Electroluminescence of doped organic thin films", J. Appl. Phys., vol. 65, No. 9 (1989), pp. 3610–3616.

Adachi, C., et al. "Electroluminescence in Organic Films with Three–Layer Structure", Japanese J. Appl. Phys., vol. 27, No. 2 (1998), pp. L269–L271.

Journal of the Chemical Society of Japan, vol. 11 (1991), pp. 1540–1548.

(List continued on next page.)

*Primary Examiner*—Cynthia H. Kelly
*Assistant Examiner*—Dawn Garrett
(74) *Attorney, Agent, or Firm*—Wenderoth, Lind & Ponack, L.L.P.

(57) ABSTRACT

Use of an organic EL device comprising a dipyridylthiophene derivative represented by the following general formula (1) has made it possible to provide an organic EL device with high luminous efficiency at low voltage. Provided that in the formula, X is S or $SO_2$, $R_5$ and $R_6$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when $R_5$ and $R_6$ each independently represent an alkenyl, alkoxy, aryl or heterocyclic group they may be bonded together but not into a benzo condensed ring, and $A_1$ and $A_2$ are independently a 2-pyridyl group or 3-pyridyl group (1)

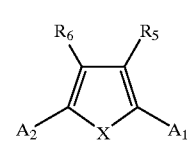

5 Claims, No Drawings

OTHER PUBLICATIONS

*Communications to the Editor*, "Stable Thiopene Sulfoxide", Journal of the American Chemical Society, vol. 92, No. 26 (1970), pp. 7610–7611.

Tanaka, H., et al., "Novel hole–transporting materials based on triphenylamine for organic electroluminescent devices", J. Chem. Soc. Chem. Commun., (1996), pp. 2175–2176.

Kuwabara, Y., et al. "Thermally Stable Multilayered Organic Electroluminescent Devices Using Novel Starburst Molecules, 4, 4', 4"–Tri(N–barbazolyl)triphenylamine (TCTA) and 4,4'4–Tris(3–methylphenylphenylamino)triphenylamine (m–MTDATA), as Hole–Transport Materials, Adv. Mater., vol. 6, No. 9 (1994), pp. 677–679.

Preprints of the $72^{nd}$ Chemical Society of Japan National Meeting, Lecture Proc. (II), p. 1392, 2PB098.

Yamaguchi, Y., et al. "Application of Unsymmetrical Diphenoquinone Derivatives to Xerography (I)—Molecular Design of a Novel Class of Polymer–dispersibles Electron––transport–active Compounds", Journal of the Society of Electrophotography of Japan, vol. 30, No. 3 (1991), pp. 266–273.

Adachi, C., et al. "Organic Electroluminescent Device with a Three–Layer Structure," Japanese J. Appl. Phys., vol. 27, No. 4 (1988), pp. L713–L715.

Adachi, C., et al. "Organic electroluminescent device having a hole conductor as an emitting layer", Appl. Phys. Lett., vol 55, No. 15 (1989), pp. 1489–1491.

Kido, J., et al. "1,2,4–Triazole Derivative as an Electron Transport Layer in Organic Electroluminescent Devices", Jpn. J. Appl. Phys., vol 32 (1993), pp. L917–L920.

Polymer Preprints, Japan, vol. 43, No. 3 (1994), (III) Pla007, p. 978.

Izumizawa, T., et al. "Study on Electroluminescent Behaviours of Metal (III)–quinolinolates", Technical Report of Institute of Electronics, Information and Communication Engineers, vol. 92, No. 311 (1992), pp. 43–48.

Fagan, P.J., et al. "Metallacycle Transfer from Zirconium to Main Group Elements: A Versatile Synthesis of Heterocycles", J. Am. Chem. Soc., vol. 116 (1994), pp. 1880–1889.

Jiang, B., et al. "General, Efficient Route to Thiopene–1–Oxides and Well–Defined, Mixed Thiopene–Thiopene–1–Oxide Oligomers", J. Am. Chem. Soc., vol. 121 (1999), pp. 9744–9745.

Yamamoto, T., et al. "Polymer Light–Emitting Diodes with Single–and Double–Layer Structures Using Poly(2,3–diphenylquinoxaline–5,8–diyl)", Jpn. Appl. Phys., vol. 33 (1994), pp. L250–L253.

Polymer Preprints, Japan, vol. 43, No. 7 (1994), 14J07, pp. 2450–2451.

Preprints of the $40^{th}$ Japan Applied Physics Related Association Meeting, Lecture Proc., (1993), p. 1146.

"Organic El Material and Display", CMC, (2001), pp. 169–173.

Baldo, M.A., et al. "Very high–efficiency green organic light–emitting devices based on electrophosphorescence", Applied Physics Letters, vol. 75, No. 1 (1999), pp. 4–6.

Baldo, M.A., et al. "Highly efficient phosporescent emission from organic electroluminescent devices", Nature, vol. 395 (1998), pp. 151–154.

Sano, T., et al. "Novel Europium Complex for Electroluminescent Devices with Sharp Red Emission", Jpn. J. Appl. Phys., vol. 34 (1995), pp. 1883–1887.

\* cited by examiner

ORGANIC ELECTROLUMINESCENT DEVICE COMPRISING DIPYRIDYLTHIOPHENE DERIVATIVE

TECHNICAL FIELD

The present invention relates to an organic electroluminescent device (hereunder abbreviated to organic EL device). More specifically, it relates to an organic EL device comprising a dipyridylthiophene derivative.

BACKGROUND ART

Recent years have seen greater attention focused on organic EL devices as next-generation full color flat panel displays, and this has led to their active research and development. Organic EL devices are injection-type EL devices which comprise a luminescent layer sandwiched between two electrodes, wherein injection of electrons and holes in the organic luminescent layer results in their recombining and consequent light emission. The materials used include low molecular materials and polymer materials, which are known to give organic EL devices with high luminance.

Two types of such organic EL devices exist. One is obtained by doping a fluorescent dye to a charge transport layer, as published by C. W. Tang et al. (J. Appl. Phys., 65, 3610(1989)), and the other employs the fluorescent dye itself alone (for example, the device described in Jpn. J. Appl. Phys. 27, L269(1988)).

The devices using fluorescent dyes as luminescent layers are largely classified into three types. The first type has three layers with a luminescent layer sandwiched between an electron transport layer and a hole transport layer, the second type has two layers with a hole transport layer and a luminescent layer laminated together, and the third type has two layers with an electron transport layer and a luminescent layer laminated together. Such multilayer structures are known to enhance the luminous efficiency of organic EL devices.

The known hole transport materials used in organic EL devices include many and various materials which are primarily triphenylamine derivatives, but few materials are known to be usable as electron transport materials. Furthermore, the existing electron transport materials have low charge transport capacity compared to known hole transport materials such as N,N'-di(1-naphthyl)-N,N'-diphenyl-4,4'-diaminobiphenyl, and when used in organic EL devices, they restrict the performance of EL devices, such that it has not been possible to achieve satisfactory device characteristics.

As specific examples of such electron transport materials there are known metal complexes of oxine derivatives (described in JP-A 59-194393 and elsewhere), 2-(4-biphenylyl)-5-(4-tert-butylphenyl)-1,3,4-oxadiazole (PBD), and the like. The former allows driving of organic EL devices at relatively low voltage, but this is still inadequate, and because the luminescence itself is green it is difficult to achieve emission of blue light. The above-mentioned organic EL device (Jpn. J. Appl. Phys. 27, L269(1988)) is an example of using the latter as an electron transport layer. However, instability of thin films, including a tendency toward crystallization, has been indicated as a problem, and therefore compounds with multiple oxadiazole rings have been developed (Journal of the Chemical Society of Japan, 11, 1540(1991), JP-A 6-145658, JP-A 6-92947, JP-A 5-152027, JP-A 5-202011, JP-A 6-136359, etc.). Nevertheless, these compounds have also exhibited properties unsuitable for practical use, such as high driving voltage. Quinoxaline derivatives have been reported as additional compounds (JP-A 6-207169). Dimerization increases molecular weight and thus enhances the stability of thin films, but still a high driving voltage has been required, and such dimers have thus been inadequate for practical use. Silacyclopentadiene derivatives have been reported as well (described in JP-A 9-87616 and elsewhere). These have been capable of driving organic EL devices at relatively low voltage, but have also been insufficient for practical use. Dibenzoxazolyl-thiophene derivatives have been reported as thiophene ring-containing compounds (JP-A 5-343184, JP-A 11-345686 and elsewhere). However, while thin-film stability is improved by introduction of substituents, the driving voltage has been too high to be adequate for practical use.

As mentioned above, the electron transport materials used in conventional organic EL devices do not meet the current demands for high performance by full color flat panel displays, and therefore superior materials have been desired in order to achieve lower voltage and higher efficiency for organic EL devices.

The present invention has been accomplished in light of these problems of the prior art, and its object is to provide a low-voltage, high-efficiency organic EL device.

As a result of diligent research directed toward solving the aforementioned problems associated with conventional organic EL devices, the present inventors have found that certain dipyridylthiophene derivatives are high performance electron transport materials which when employed can give low-voltage, high-efficiency organic EL devices, and the present invention has thus been completed.

DISCLOSURE OF THE INVENTION

In other words, the present invention has the following construction.

A first aspect of the invention is an organic electroluminescent device characterized by comprising a dipyridylthiophene derivative represented by the following general formula (1):

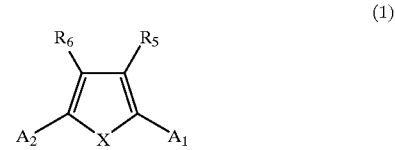

(1)

where X is S or $SO_2$, $R_5$ and $R_6$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when $R_5$ and $R_6$ each independently represent an alkenyl, alkoxy, aryl or heterocyclic group they may be bonded together but not into a benzo condensed ring, and $A_1$ and $A_2$ are independently represented by the following formula (2) or (3):

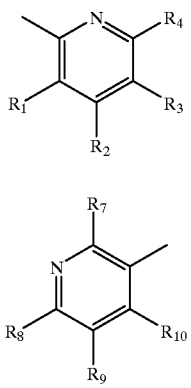

(2)

(3)

where $R_1$–$R_4$ and $R_7$–$R_{10}$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when they are each independently an alkenyl, alkoxy, aryl or heterocyclic group and are adjacent, they may be bonded together.

According to a preferred mode of the invention, both $A_1$ and $A_2$ in general formula (1) are groups represented by general formula (2).

According to another preferred mode of the invention, both $A_1$ and $A_2$ in general formula (1) are groups represented by general formula (3).

According to still another preferred mode of the invention, $A_1$ in general formula (1) is a group represented by general formula (2) and $A_2$ is a group represented by general formula (3).

Still another preferred mode of the invention is an organic electroluminescent device wherein the dipyridylthiophene derivative represented by general formula (1) is contained in an electron transport layer.

Still another preferred mode of the invention is an organic electroluminescent device wherein the dipyridylthiophene derivative represented by general formula (1) is contained in a luminescent layer.

A second aspect of the invention is an electron transport material comprising a dipyridylthiophene derivative represented by general formula (1).

A third aspect of the invention is a luminescent material comprising a dipyridylthiophene derivative represented by general formula (1).

PREFERRED MODES OF THE INVENTION

The present invention will now be explained in further detail. In general formulas (1), (2) and (3), X is S or $SO_2$, and $R_1$ to $R_{10}$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group.

As examples of the alkyl groups there may be mentioned methyl, ethyl, n-propyl, isopropyl, n-butyl, sec-butyl, tert-butyl, n-pentyl, n-hexyl, cyclopropyl, cyclobutyl, cyclopentyl and cyclohexyl. As examples of the alkenyl groups there may be mentioned vinyl, allyl, 1-propenyl, 1,3-butadienyl, 2-pentenyl, and 2-hexenyl, as examples of the alkoxy groups there may be mentioned methoxy, ethoxy and propoxy, and as examples of the aryloxy groups there may be mentioned phenyloxy and naphthyloxy. As examples of the aryl groups there may be mentioned phenyl and naphthyl, and as examples of the heterocyclic groups there may be mentioned thiophene, benzoxazole, benzothiazole, pyridine, quinoline and phenanthroline.

When $R_1$ to $R_{10}$ each independently represent an alkenyl, alkoxy, aryl or heterocyclic group and are adjacent, they may be bonded together, but excluding a benzo condensed ring formed by $R_5$ and $R_6$.

Of the compounds represented by general formula (1), some will have a plurality of $R_1$ to $R_4$ groups or a plurality of $R_7$ to $R_{10}$ groups, but in such cases as well, each $R_1$ to $R_4$ or each $R_7$ to $R_{10}$ independently represents the aforementioned atom or groups.

The following may be mentioned as specific examples of dipyridylthiophene derivatives to be used for the invention.

2,3,4,5-tetra(2-pyridyl)thiophene,
2,5-di(3-pyridyl)-3,4-di(2-pyridyl)thiophene,
2-(2-pyridyl)-3,4-di(2-pyridyl)-5-(3-pyridyl)thiophene,
2,5-di(2-pyridyl)-3,4-diphenylthiophene,
2,5-di(3-pyridyl)-3,4-diphenylthiophene,
2,5-bis(6-(2-pyridyl)-2-pyridyl)-3,4-diphenylthiophene,
2,5-bis(6-(2-pyridyl)-3-pyridyl)-3,4-diphenylthiophene,
2-(6-(2-pyridyl)-2-pyridyl)-3,4-diphenyl-5-(6-(2-pyridyl)-3-pyridyl)thiophene,
2,5-bis(6-(2-benzoxazolyl)-2-pyridyl)-3,4-diphenylthiophene,
2,5-bis(6-(2-benzoxazolyl)-3-pyridyl)-3,4-diphenylthiophene,
2-(6-(2-benzoxazolyl)-2-pyridyl)-3,4-diphenyl-5-(6-(benzoxazolyl)-3-pyridyl)thiophene,
2,5-bis(6-(2-benzothiazolyl)-2-pyridyl)-3,4-diphenylthiophene,
2,5-bis(6-(2-benzothiazolyl)-3-pyridyl)-3,4-diphenylthiophene,
2-(6-(2-benzothiazolyl)-2-pyridyl)-3,4-diphenyl-5-(6-(benzothiazolyl)-3-pyridyl)thiophene,
2,5-bis(6-(3-quinolyl)-2-pyridyl)-3,4-diphenylthiophene,
2,5-bis(6-(3-quinolyl)-3-pyridyl)-3,4-diphenylthiophene,
2-(6-(2-quinolyl)-2-pyridyl)-3,4-diphenyl-5-(6-(quinolyl)-3-pyridyl)thiophene,
2,5-di(2-quinolyl)-3,4-diphenylthiophene,
2,5-di(3-quinolyl)-3,4-diphenylthiophene,
2,5-di(4-isoquinolyl)-3,4-diphenylthiophene,
2,5-di(2-(1,10-phenanthryl))-3,4-diphenylthiophene,
2,5-di(3-(1,10-phenanthryl))-3,4-diphenylthiophene,
2,5-di(2-pyridyl)-3,4-dimethylthiophene,
2,5-di(3-pyridyl)-3,4-dimethylthiophene,
2,5-bis(6-(2-pyridyl)-2-pyridyl)-3,4-ditertiary-butylthiophene,
2,5-bis(6-(2-pyridyl)-3-pyridyl)-3,4-ditertiary-butylthiophene,
2,5-bis(6-(2-pyridyl)-2-pyridyl)-3,4-di(2-pyridyl)thiophene,
2,5-bis(6-(2-pyridyl)-3-pyridyl)-3,4-di(2-pyridyl)thiophene,
2,5-bis(6-(2-pyridyl)-2-pyridyl)-3,4-ethylenedioxythiophene,
2,5-bis(6-(2-pyridyl)-3-pyridyl)-3,4-ethylenedioxythiophene,
2-(6-(2-pyridyl)-2-pyridyl)-3,4-ethylenedioxy-5-(6-(2-pyridyl)-3-pyridyl)thiophene,
2,5-bis(6-(2-pyridyl)-2-pyridyl)-3,4-trimethylenethiophene,
2,5-bis(6-(2-pyridyl)-3-pyridyl)-3,4-trimethylenethiophene,
2-(6-(2-pyridyl)-2-pyridyl)-3,4-trimethylene-5-(6-(2-pyridyl)-3-pyridyl)thiophene,
2,2',5,5'-tetra(2-pyridyl)-3,3'-bithiophene,
2,2',5,5'-tetra(3-quinolyl)-3,3'-bithiophene, 2,3,4,5-tetra(2-pyridyl)thiophene-1,1-dioxide,
2,3,4,5-tetra(3-pyridyl)thiophene-1,1-dioxide,
2,5-bis(6-(2-pyridyl)-2-pyridyl)-3,4-diphenylthiophene-1,1-dioxide,
2,5-bis(6-(2-pyridyl)-3-pyridyl)-3,4-diphenylthiophene-1,1-dioxide,
2-(6-(2-pyridyl)-2-pyridyl)-3,4-diphenyl-5-(6-(2-pyridyl)-3-pyridyl)thiophene-1,1-dioxide,
2,5-bis(6-(2-pyridyl)-2-pyridyl)-3,4-ethylenedioxythiophene-1,1-dioxide,
2,5-bis(6-(2-pyridyl)-3-pyridyl)-3,4-ethylenedioxythiophene-1,1-dioxide,
2,5-bis(6-(2-pyridyl)-2-pyridyl)-3,4-trimethylenethiophene-1,1-dioxide, and
2,5-bis(6-(2-pyridyl)-3-pyridyl)-3,4-trimethylenethiophene-1,1-dioxide.

These compounds can be synthesized by known processes, such as the process described in J. Am. Chem. Soc., 116, 1880(1994), the process described in J. Am. Chem. Soc., 121, 9744(1999), the process described in J. Am. Chem. Soc., 92, 7610(1970), or the processes described in the synthesis examples of the present specification.

These dipyridylthiophene derivatives are suitable as materials for formation of electron transport layers, with which the organic EL device of the invention can operate at low voltage and high efficiency. This is due to the excellent electron transport properties of the dipyridylthiophene derivatives represented by general formula (1) and (2) used for the invention. Moreover, since the dipyridylthiophene derivatives themselves are luminescent, they are also suitable as luminescent materials for organic EL devices.

Various modes may be mentioned for the structure of the organic EL device of the invention, but the basic structure has an organic layer containing the dipyridylthiophene derivative sandwiched between a pair of electrodes (anode and cathode), and if desired, a hole transport layer, a luminescent layer or an electron transport layer made of another material may be combined with the dipyridylthiophene derivative layer. When used as an electron transport layer, another material may be used in combination to further enhance the function.

As concrete constructions there may be mentioned multilayer structures such as (1) anode/hole transport layer/dipyridylthiophene derivative layer/cathode, (2) anode/hole transport layer/luminescent layer/dipyridylthiophene derivative layer/cathode and (3) anode/hole transport layer/dipyridylthiophene derivative layer/electron transport layer/cathode.

The organic EL device of the invention having any of the aforementioned structures is preferably supported on a substrate. The substrate may be any one with mechanical strength, thermal stability and transparency, among which glass, transparent plastic films and the like may be used. The anode material for the organic EL device of the invention may be a metal, alloy, electric conductive compound or mixture thereof having a work function of greater than 4 eV. Specifically there may be mentioned metals such as Au, and conductive transparent materials such as CuI, indium tin oxide (hereunder abbreviated to ITO), $SnO_2$, ZnO and the like.

The cathode substance may be a metal, alloy, electric conductive compound or mixture thereof having a work function of less than 4 eV. Specifically there may be mentioned aluminum, calcium, magnesium, lithium, magnesium alloy, aluminum alloy or the like, where alloys include aluminum/lithium fluoride, aluminum/lithium, magnesium/silver, magnesium/indium, etc. In order to bring out efficient luminescence of the organic EL device, at least one of the electrodes preferably has a light transmittance of 10% or greater. The sheet resistance of the electrode is preferably no greater than a few hundred $\Omega/\square$. The film thickness will depend on the nature of the electrode material, but it is normally selected in the range of 10 nm to 1 $\mu$m, and preferably 10–400 nm. Such electrodes can be fabricated by using the aforementioned electrode substances to form thin-films by a method such as vapor deposition or sputtering.

For the other hole transport material used in the organic EL device of the invention there may be selected materials that are commonly used in the prior art as hole charge transport materials for photoconductive materials, or any publicly known materials used in hole injection layers and hole transport layers of organic EL devices. As examples there may be mentioned carbazole derivatives (N-phenylcarbazole, polyalkylenecarbazole, etc.), triarylamine derivatives (TPD, polymers with aromatic tertiary amines as main chains or side chains, 1,1-bis(4-di-p-tolylaminophenyl)cyclohexane, N,N'-diphenyl-N,N'-dinaphthyl-4,4'-diaminobiphenyl, 4,4',4"-tris{N-(3-methylphenyl)-N-phenylamino}triphenylamine, the compounds described in J. Chem. Soc. Chem. Comm., 2175 (1996), the compounds described in JP-A 57-144558, JP-A 61-62038, JP-A 61-124949, JP-A 61-134354, JP-A 61-134355, JP-A 61-112164, JP-A 4-308688, JP-A 6-312979, JP-A 6-267658, JP-A 7-90256, JP-A 7-97355, JP-A 6-1972, JP-A 7-126226, JP-A 7-126615, JP-A 7-331238, JP-A 8-100172 and JP-A 8-48656, the starburst amine derivatives described in Adv. Mater., 6, 677 (1994), etc.), stilbene derivatives (those described in Preprints of 72nd National Meeting of the Chemical Society of Japan (II), p.1392, 2PB098, etc.), phthalocyanine derivatives (non-metals, copper phthalocyanine, etc.), polysilanes, and the like.

There are no particular restrictions on the other electron transport materials to be used in the organic EL device of the invention, and there may be selected for use materials that are commonly used in the prior art as electron transferring compounds for photoconductive materials, or any publicly known materials used in electron injection layers and electron transport layers of organic EL devices. As preferred examples of such electron transferring compounds there may be mentioned diphenylquinone derivatives (those described in Journal of the Society of Electrophotography of Japan, 30(3), 266 (1991), etc.), perylene derivatives (those described in J. Appl. Phys., 27, 269 (1988), etc.), oxadiazole derivatives (those described in Jpn. J. Appl. Phys., 27, L713 (1988), Appl. Phys. Lett., 55, 1489 (1989), etc.), thiophene derivatives (those described in JP-A 4-212286, etc.), triazole derivatives (those described in Jpn. J. Appl. Phys., 32, L917 (1993), etc.), thiadiazole derivatives (those described in Polymer Preprints, Japan, 43, (III), Pla007, etc.), metal complexes of oxine derivatives (those described in Technical Report of the Institute of Electronics, Information and Communication Engineers, 92(311), 43 (1992), etc.), polymers of quinoxaline derivatives (those described in Jpn. J. Appl. Phys., 33, L250(1994), etc.), phenanthroline derivatives (those described in Polymer Preprints, Japan, 43, 14J07, etc.) and silacyclopentadiene derivatives (those described in JP-A 9-87616, etc.).

The electron transport layer in the organic EL device of the invention may be composed of a single layer comprising a dipyridylthiophene compound according to the invention and/or at least one of the aforementioned compounds, or it may consist of a laminate of multiple layers comprising different types of compounds. The electron transport layer may also be fabricated by dispersing a dipyridylthiophene compound according to the invention in a polymer material.

Other luminescent materials which may be used in the luminescent layer for the organic EL device of the invention include publicly known luminescent materials such as the daylight fluorescent materials, fluorescent brighteners, laser dyes, organic scintillators and various fluorescent analysis reagents described in the Polymer Functional Material Series, "Photofunctional Materials", ed. by Society of Polymer Science, Japan, Kyoritsu Publishing, (1991), P236. Specifically preferred are polycyclic condensation compounds such as anthracene, phenanthrene, pyrene, chrysene, perylene, coronene, rubrene and quinacridone, oligophenylene compounds such as quarterphenyl, scintillators for liquid scintillation such as 1,4-bis(2-methylstyryl)benzene, 1,4-bis(4-methylstyryl)benzene, 1,4-bis(4-phenyl-5-oxazolyl)benzene, 1,4-bis(5-phenyl-2-oxazolyl)benzene, 2,5-bis(5-tertiary-butyl-2-benzoxazolyl)thiophene, 1,4-diphenyl-1,3-butadiene, 1,6-diphenyl-1,3,5-hexatriene and 1,1,4,4-tetraphenyl-1,3-butadiene, the metal complexes of oxine derivatives described in JP-A 63-264692, coumarin dyes, dicyanomethylenepyrane dyes, dicyanomethylenethiopyrane dyes, polymethine dyes, oxobenzanthracene dyes, xanthene dyes, carbostyryl dyes and perylene dyes, the oxazine compounds described in German Patent No. 2,534,713, the stilbene derivatives described in Preprints of the 40th Annual Meeting of the Japan Society of Applied Physics, 1146(1993), the spiro compounds described in JP-A 7-278537 and the oxadiazole compounds described in JP-A 4-363891. The publicly known phosphorescent materials described in "Organic EL materials and displays", CMC, p. 170 may also be used in the luminescent layer of the organic EL device of the invention. Specifically there may be mentioned indium complexes (those described in Appl. Phys. Lett., 75, 4(1999), etc.), platinum complexes (those described in Nature, 395, 151(1998), etc.), europium complexes (those described in Jpn. J. Appl. Phys., 34, 1883 (1995), etc.) and the like.

Each of the layers constituting the organic EL device of the invention may be formed by creating a thin-film using the material for each layer by a publicly known method such as vapor deposition, spin coating, casting or the like. The film thickness of each layer formed in this manner is not particularly restricted and may be appropriately selected depending on the nature of the material, but it is normally selected in the range of 2–5000 nm. Vapor deposition is preferably used as the method for forming a thin-film of the dipyridylthiophene derivative alone from the standpoint of easily obtaining a homogeneous film and inhibiting production of pinholes. When vapor deposition is used to form the thin-film, the vapor deposition conditions will differ depending on the type of dipyridylthiophene derivative, the crystalline and association structure desired for the molecular accumulation film, etc., but in most cases it is preferred to appropriately select a boat heating temperature of 50–400° C., a vacuum degree of $10^{-6}$ to $10^{-3}$ Pa, a vapor deposition rate of 0.01–50 nm/sec, a substrate temperature of −150° C. to +300° C. and a film thickness in the range of 5 nm to 5 µm.

A method of fabricating an organic EL device comprising the above-mentioned anode/hole transport layer/luminescent layer/dipyridylthiophene derivative/cathode structure will now be explained as an example of a method of fabricating an organic EL device using a dipyridylthiophene derivative according to the invention. After making the anode by forming a thin-film composed of the anode substance onto an appropriate substrate by vapor deposition to a film thickness of no greater than 1 µm and preferably in the range of 10–200 nm, the hole transport layer is formed on this anode to a film thickness of no greater than 1 µm, the luminescent layer is formed on the hole transport layer to a film thickness of no greater than 1 µm, a thin-film of the dipyridylthiophene derivative is formed on the luminescent layer to prepare the electron transport layer, and then a thin-film composed of the cathode substance is formed by vapor deposition to a film thickness of no greater than 1 µm to make the cathode, thereby obtaining the intended organic EL device. For fabrication of the organic EL device, the order of formation may be reversed, forming the cathode, electron transport layer, luminescent layer, hole transport layer and anode in that order.

When a direct current voltage is to be applied to the organic EL device obtained in this manner, the polarity of application may be + for the anode and − for the cathode, and application of a voltage of approximately 2–40 V will allow luminescence from the transparent or semi-transparent electrode side (anode or cathode, or both). The organic EL device also emits light upon application of an alternating current voltage. The applied alternating current may have any desired waveform.

EXAMPLES

The present invention will now be explained in further detail by way of examples.

Synthesis Example 1

Synthesis of 2,5-bis(6-(2-pyridyl)-2-pyridyl)-3,4-diphenylthiophene (hereunder abbreviated to BPPDPT)

After placing 3.5 g of 3,4-diphenylthiophene and 60 ml of tetrahydrofuran in a flask and cooling to −30° C. in an argon atmosphere, 11 ml of a 1.5 mol/l concentration n-butyllithium/n-hexane solution was added dropwise. The mixture was stirred at −30° C. for 2 hours, and then 4.1 g of a zinc chloride/tetramethylethylenediamine complex was added before raising the temperature to room temperature. After stirring for 30 minutes, 3.8 g of 2-bromo-6-(2-pyridyl) pyridine and 0.52 g of a palladium chloride/bistriphenylphosphine complex were added and the mixture was stirred for 2 hours at reflux temperature. After completion of the reaction, the product was cooled to room temperature, purified water was added, the organic layer was extracted, and the concentrate obtained using an evaporator was purified by recrystallization to obtain 4.5 g of 2-(6-(2-pyridyl)-2-pyridyl)-3,4-diphenylthiophene. After placing 3.3 g of the 2-(6-(2-pyridyl)-2-pyridyl)-3,4-diphenylthiophene and 80 ml of tetrahydrofuran in a flask and cooling to −30° C. in an argon atmosphere, 6.2 ml of a 1.5 mol/l concentration n-butyllithium/n-hexane solution was added dropwise. The mixture was stirred at −30° C. for 2 hours, and then 2.4 g of a zinc chloride/tetramethylethylenediamine complex was added before raising the temperature to room temperature. After stirring for 30 minutes, 2.2 g of 2-bromo-6-(2-pyridyl)pyridine and 0.30 g of a palladium chloride/bistriphenylphosphine complex were added and the mixture was stirred for 2 hours at reflux temperature. After completion of the reaction, the product was cooled to room temperature, purified water was added, and the organic layer was extracted. The organic layer was concentrated with an evaporator and purified by column chromatography and recrystallization to obtain 1.1 g of BPPDPT.

1H-NMR (CDCl$_3$) δ=8.6–8.7 (m, 2H), 8.4–8.5 (m, 2H), 8.2–8.3 (dd, 2H), 7.8–7.9 (m, 2H), 7.5–7.6 (t, 2H), 7.3–7.4 (m, 2H), 7.2–7.3 (m, 6H), 7.1–7.2 (m, 4H), 6.8–6.9 (dd, 2H)

Example 1

A 25 mm×75 mm×1.1 mm glass panel with ITO vapor deposited to a thickness of 50 nm (manufactured by Tokyo Sanyo Vacuum Industries Co., Ltd.) was used as a transparent support substrate. The transparent support substrate was set in the substrate holder of a commercially available vapor deposition apparatus (manufactured by Sinku Kiko Co., Ltd.), and a molybdenum vapor deposition boat containing N,N'-dinaphthyl-N,N'-diphenyl-4,4'-diaminobiphenyl (hereunder abbreviated to NPD), a molybdenum vapor deposition boat containing 9-dimesitylborylanthracene (hereunder abbreviated to DMBA), a molybdenum vapor deposition boat containing BPPDPT, a molybdenum vapor deposition boat containing lithium fluoride and a tungsten vapor deposition boat containing aluminum were mounted thereon. The pressure of the vacuum vessel was reduced to 1×10$^{-3}$ Pa, the NPD-containing vapor deposition boat was heated for vapor deposition of NPD to a film thickness of 50 nm to form a hole transport layer, and then the DMBA-containing vapor deposition boat was heated for vapor deposition of DMBA to a film thickness of 30 nm to form a luminescent layer. The BPPDPT-containing vapor deposition boat was then heated for vapor deposition of BPPDTP to a film thickness of 20 nm to form an electron transport layer. The vapor deposition rate was 0.1–0.2 nm/sec. Next, the lithium fluoride-containing vapor deposition boat was heated for vapor deposition to a film thickness of 0.5 nm at a vapor deposition rate of 0.003–0.01 nm/sec, and then the aluminum-containing vapor deposition boat was heated for vapor deposition to a film thickness of 100 nm at a vapor deposition rate of 0.2–0.5 nm/sec, to obtain an organic EL device. Using an ITO electrode as the anode and a lithium fluoride/aluminum electrode as the cathode, a direct current voltage of approximately 4 V was applied resulting in a current flow of approximately 8 mA/cm$^2$, to obtain blue luminescence with a wavelength of 460 nm at a luminance of 100 cd/m$^2$ and a luminous efficiency of approximately 1 lm/W.

Comparative Example 1

An organic EL device was obtained in the same manner as Example 1 except that aluminum tris(8-hydroxyquinoline) (hereunder abbreviated to ALQ) was used instead of BPPDPT. Using an ITO electrode as the anode and a lithium fluoride/aluminum electrode as the cathode, a direct current voltage of approximately 6 V was applied resulting in a current flow of approximately 10 mA/cm$^2$, to obtain blue luminescence with a wavelength of 460 nm at a luminance of 100 cd/m$^2$ and a luminous efficiency of approximately 0.2 lm/W.

Example 2

An organic EL device was obtained in the same manner as Example 1 except that ALQ was used instead of DMBA.

Using an ITO electrode as the anode and a lithium fluoride/aluminum electrode as the cathode, a direct current voltage of approximately 4 V was applied resulting in a current flow of approximately 4 mA/cm$^2$, to obtain green luminescence with a wavelength of 520 nm at a luminance of approximately 100 cd/m$^2$ and a luminous efficiency of approximately 2 lm/W.

Example 3

A 25 mm×75 mm×1.1 mm glass panel with ITO vapor deposited to a thickness of 50 nm (manufactured by Tokyo Sanyo Vacuum Industries Co., Ltd.) was used as a transparent support substrate. The transparent support substrate was set in the substrate holder of a commercially available vapor deposition apparatus (manufactured by Sinku Kiko Co., Ltd.), and a molybdenum vapor deposition boat containing NPD, a molybdenum vapor deposition boat containing BPPDPT, a molybdenum vapor deposition boat containing lithium fluoride and a tungsten vapor deposition boat containing aluminum were mounted thereon. The pressure of the vacuum vessel was reduced to 1×10$^{-3}$ Pa, the NPD-containing vapor deposition boat was heated for vapor deposition of NPD to a film thickness of 50 nm to form a hole transport layer, and then the BPPDPT-containing vapor deposition boat was heated for vapor deposition of BPPDTP to a film thickness of 50 nm to form a luminescent layer. The vapor deposition rate was 0.1–0.2 nm/sec. Next, the lithium fluoride-containing vapor deposition boat was heated for vapor deposition to a film thickness of 0.5 nm at a vapor deposition rate of 0.003–0.01 nm/sec, and then the aluminum-containing vapor deposition boat was heated for vapor deposition to a film thickness of 100 nm at a vapor deposition rate of 0.2–0.5 nm/sec, to obtain an organic EL device. Using an ITO electrode as the anode and a lithium fluoride/aluminum electrode as the cathode, a direct current voltage of approximately 7 V was applied resulting in a current flow of approximately 50 mA/cm$^2$, to obtain blue luminescence. The luminescent spectrum matched the luminescent spectrum of a BPPDPT vapor deposition film, and the emission wavelength was 430 nm.

Synthesis Example 2

Synthesis of 2,5-bis(6-(2-pyridyl)-2-pyridyl)-3,4-ethylenedioxythiophene (hereunder abbreviated to BPPEOT)

There was obtained 0.68 g of BPPEOT by exactly the same procedure as in Synthesis Example 1, except that 3,4-ethylenedioxythiophene was used instead of 3,4-diphenylthiophene.

1H-NMR (CDCl$_3$) δ=8.6–8.7 (m, 4H), 8.2–8.3 (d, 2H), 8.0–8.1 (d, 2H), 7.8–7.9 (m, 2H), 7.9–8.0 (t, 2H), 7.3–7.4 (m, 2H), 4.5 (s, 4H)

Example 4

A 25 mm×75 mm×1.1 mm glass panel with ITO vapor deposited to a thickness of 50 nm (manufactured by Tokyo Sanyo Vacuum Industries Co., Ltd.) was used as a transparent support substrate. The transparent support substrate was set in the substrate holder of a commercially available vapor deposition apparatus (manufactured by Sinku Kiko Co., Ltd.), and a molybdenum vapor deposition boat containing NPD, a molybdenum vapor deposition boat containing ALQ, a molybdenum vapor deposition boat containing BPPEOT, a molybdenum vapor deposition boat containing lithium fluoride and a tungsten vapor deposition boat containing aluminum were mounted thereon. The pressure of the vacuum vessel was reduced to 1×10$^{-3}$ Pa, the NPD-containing vapor deposition boat was heated for vapor deposition of NPD to a film thickness of 50 nm to form a hole transport layer, and then the ALQ-containing vapor deposition boat was heated for vapor deposition of ALQ to a film thickness of 30 nm to form a luminescent layer. The BPPEOT-containing vapor deposition boat was then heated for vapor deposition of BPPEOT to a film thickness of 20 nm to form an electron transport layer. The vapor deposition rate was 0.1–0.2 nm/sec. Next, the lithium fluoride-containing vapor deposition boat was heated for vapor deposition to a film thickness of 0.5 nm at a vapor deposition rate of 0.003–0.01 nm/sec, and then the aluminum-containing vapor deposition boat was heated for vapor deposition to a film thickness of 100 nm at a vapor deposition rate of 0.2–0.5 nm/sec, to obtain an organic EL device. Using an ITO electrode as the anode and a lithium fluoride/aluminum electrode as the cathode, a direct current voltage of approximately 3 V was applied resulting in a current flow of approximately 4 mA/cm², to obtain green luminescence with a wavelength of 520 nm at a luminance of approximately 100 cd/m² and a luminous efficiency of approximately 2 lm/W.

Synthesis Example 3

Synthesis of 2,5-bis(6-(2-pyridyl)-3-pyridyl)-3,4-diphenylthiophene (hereunder abbreviated to BP3PDPT)

After placing 0.49 g of magnesium and 5 ml of tetrahydrofuran in a flask and dropwise adding 65 ml of a tetrahydrofuran solution containing 3.9 g of 2,5-dibromo-3,4-diphenylthiophene at room temperature in an argon atmosphere, the mixture was heated to reflux temperature. After stirring for 3 hours, it was cooled to −78° C., 70 ml of a tert-butyl methyl ether solution containing 2.2 ml of trimethylborate was added dropwise, and the temperature of the mixture was raised to room temperature. After stirring for 15 hours, the solvent was distilled off, and 75 ml of toluene, 25 ml of ethanol, 4.7 g of 2-(2-pyridyl)-5-bromopyridine, 0.69 g of palladium/tetrakistriphenylphosphine complex and 4.2 g of sodium carbonate were added prior to stirring for 6 hours at reflux temperature. After completion of the reaction, the product was cooled to room temperature, purified water was added, and the organic layer was extracted. The organic layer was concentrated with an evaporator and purified by column chromatography and recrystallization to obtain 0.78 g of BP3PDPT.

1H-NMR (CDCl₃) δ=8.6–8.7 (m, 4H), 8.3–8.4 (d, 2H), 8.2–8.3 (d, 2H), 7.7–7.9 (m, 2H), 7.5–7.7 (dd, 2H), 7.2–7.4 (m, 2H), 7.1–7.2 (m, 6H), 6.9–7.1 (m, 4H)

Example 5

An organic EL device was obtained in the same manner as Example 4 except that PB3PDPT was used instead of BPPEOT. Using an ITO electrode as the anode and a lithium fluoride/aluminum electrode as the cathode, a direct current voltage of approximately 3 V was applied resulting in a current flow of approximately 5 mA/cm², to obtain green luminescence with a wavelength of 520 nm at a luminance of approximately 100 cd/m² and a luminous efficiency of approximately 2 lm/W.

Example 6

An organic EL device was obtained in the same manner as Example 3 except that PB3PDPT was used instead of BPPDPT. Using an ITO electrode as the anode and a lithium fluoride/aluminum electrode as the cathode, a direct current voltage of approximately 6 V was applied resulting in a current flow of approximately 50 mA/cm², to obtain blue luminescence. The luminescent spectrum matched the luminescent spectrum of a BP3PDPT vapor deposition film, and the emission wavelength was 455 nm.

Industrial Applicability

As explained above, the dipyridylthiophene derivatives of the invention have excellent electron transport properties, and their use as electron transport materials or luminescent materials for organic EL devices can help provide organic EL devices with low voltage and high efficiency. That is, the organic EL devices according to the invention employing dipyridylthiophene derivatives as organic layers exhibit low operating voltage, high efficiency and satisfactory full color properties. The organic EL devices of the invention can therefore be used to fabricate high-efficiency display devices, such as full color displays.

What is claimed is:

1. An organic electroluminescent device comprising an electron transport layer containing a dipyridylthiophene derivative represented by the following general formula (1):

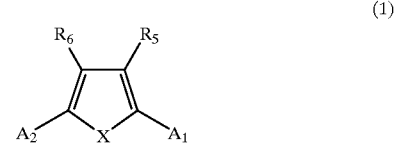

where X is S or SO₂, R₅ and R₆ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when R₅ and R₆ each independently represent an alkenyl, alkoxy, aryl or heterocyclic group they may be bonded together but not into a benzo condensed ring, and A₁ and A₂ are independently represented by the following formula (2) or (3):

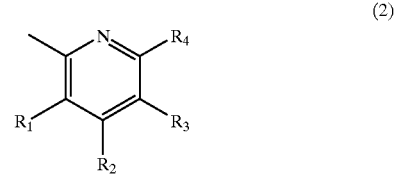

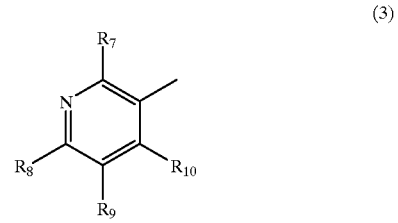

where R₁–R₄ and R₇–R₁₀ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when they are each independently an alkenyl, alkoxy, aryl or heterocyclic group and are adjacent, they may be bonded together.

2. An organic electroluminescent device according to claim 1, wherein in general formula (1), both A₁ and A₂ are groups represented by general formula (2).

3. An organic electroluminescent device according to claim 1, wherein in general formula (1), both $A_1$ and $A_2$ are groups represented by general formula (3).

4. An organic electroluminescent device according to claim 1, wherein in general formula (1), $A_1$ is a group represented by general formula (2) and $A_2$ is a group represented by general formula (3).

5. An organic electroluminescent device comprising a luminescent layer containing a dipyridylthiophene derivative represented by general formula (1):

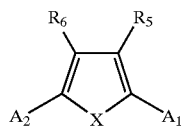

(1)

where X is S or $SO_2$, $R_5$ and $R_6$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when $R_5$ and $R_6$ each independently represent an alkenyl, alkoxy, aryl or heterocyclic group they may be bonded together but not into a benzo condensed ring, and $A_1$ and $A_2$ are independently represented by the following formula (2) or (3):

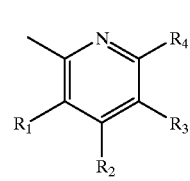

(2)

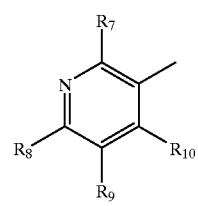

(3)

where $R_1$–$R_4$ and $R_7$–$R_{10}$ each independently represent a hydrogen atom, an alkyl group of 1–6 carbons, an alkenyl group of 2–6 carbons, an alkoxy group of 1–6 carbons, an aryloxy group, a substituted or unsubstituted aryl group or a substituted or unsubstituted heterocyclic group, with the proviso that when they are each independently an alkenyl, alkoxy, aryl or heterocyclic group and are adjacent, they may be bonded together, with the proviso that $R_3$ and $R_4$ cannot be bonded together to form a six carbon ring.

* * * * *